United States Patent [19]

Miller, deceased et al.

[11] Patent Number: 4,523,808
[45] Date of Patent: Jun. 18, 1985

[54] WELDING HELMETS WITH AUXILIARY OPTICAL VISION SYSTEMS

[75] Inventors: Charles G. Miller, deceased, late of Pasadena, by Ann S. Miller, executrix; James B. Stephens, La Crescenta; Charles Youngberg, Altadena, all of Calif.

[73] Assignee: Wilson Sales Company, Inc., South El Monte, Calif.

[21] Appl. No.: 513,112

[22] Filed: Jul. 12, 1983

[51] Int. Cl.³ .................. G02B 25/04; G02B 7/02; A61F 9/06
[52] U.S. Cl. .................... 350/146; 350/321; 350/575; 350/1.1
[58] Field of Search .............. 350/321, 311, 575, 319, 350/145, 146, 453, 1.1; 2/8, 447, 430

[56] References Cited

U.S. PATENT DOCUMENTS

| | | | |
|---|---|---|---|
| 2,249,239 | 7/1941 | Goldsmith | 2/8 |
| 2,628,530 | 2/1953 | Rabben | 350/146 |
| 2,777,129 | 1/1957 | Hummel | 2/8 |
| 3,112,490 | 12/1963 | Malcom | 350/1.1 |
| 3,522,983 | 8/1970 | Daniels | 350/145 |
| 3,868,727 | 3/1975 | Paschall | 2/8 |
| 4,330,177 | 5/1982 | Miller et al. | 350/311 |

Primary Examiner—Jon W. Henry
Attorney, Agent, or Firm—Donald D. Mon

[57] ABSTRACT

A welding helmet with welder's glass includes one or more reducing auxiliary vision systems providing viewing of areas which would otherwise be blocked by opaque portions of the welding helmet.

17 Claims, 4 Drawing Figures

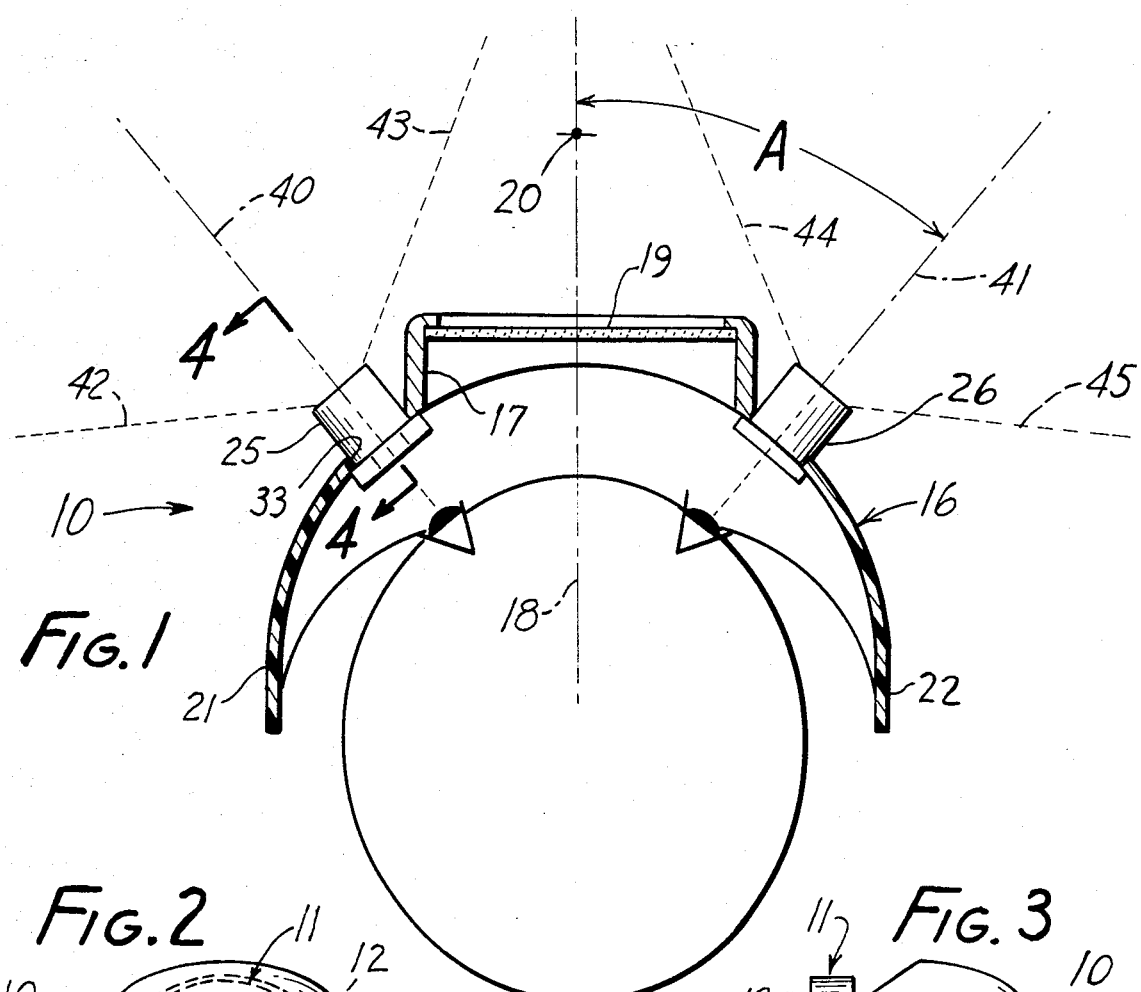
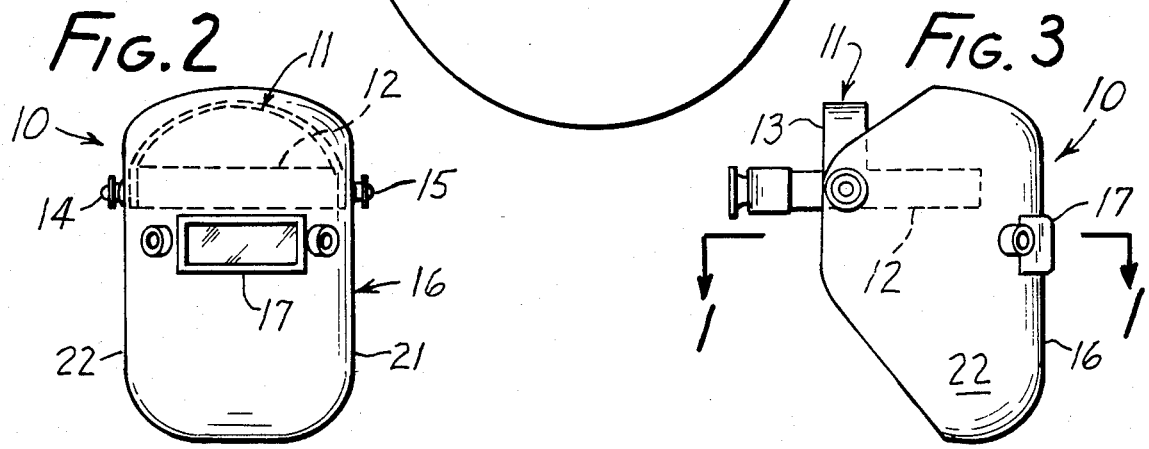
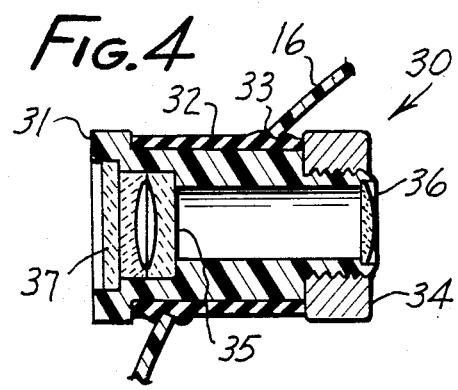

WELDING HELMETS WITH AUXILIARY OPTICAL VISION SYSTEMS

FIELD OF THE INVENTION

This invention relates to welding helmets worn by welders to protect them against welding arcs, sparks, and flames.

BACKGROUND OF THE INVENTION

The conventional welder's helmet includes a headband that fits around the forehead of the welder. An opaque shell or hood is pivotally mounted to the headband so that it can be pulled down in front of the welder's face, or pushed up out of his line of sight. A sight window is formed in the middle of the shell in front of the welder's eyes while he makes a weld or cut. A welder's filter glass is fitted into the window. This is an especially formulated glass which filters out the dangerous wavelengths from the arc or flame, and also reduces the total transmissivity of light so that only a small amount of the very intense light is passed by the filter glass. One common formulation of glass for this purpose is called "Crook's Glass".

The sight window is generally made only large enough for the welder to see the immediate area where the arc or flame is applied. The remainder of the hood is opaque and impedes the welder's view in his forward line of sight, and also in the area where he would usually enjoy peripheral vision, and which for his safety he should have.

The filter glass is very dark, so that the welder can look directly at the arc or flame, and at the molten metal which they create. These are very intense light sources, so it is not surprising that in order to enable this essential function, their transmission is so reduced that the welder cannot effectively see anything which is under ordinary or under merely very bright illumination, such as shop or floodlight illumination. For this reason, this shell is pivotally mounted. Then the welder can pivot the shell up out of the way and see his work in the ordinary light. This enables him to make his set-ups and to inspect his work, and locate himself and his equipment relative to the set-up.

There are very objectionable consequences to this conventional arrangement. One is that when the welder drops the shell in front of his eyes (usually by sharply nodding his head) he is momentarily disoriented because he does not dare to strike his arc or light the flame until his eyes are protected. As another objection, his side and peripheral vision are cut-off by the shell so that he is unable to react to or to protect himself from events which may be occurring around him. For example, he should be aware of objects moving in a direction to strike him or the presence of another person who should not be present when the welder strikes his arc or lights his flame, and the shell blocks these off.

Still another problem is that, when the welder raises the shell, it may be that a nearby arc or flame of a co-worker will be initiated. Then the glare might strike his eyes from the side, to his vision detriment.

Quite apart from the above and other risky situations, welders will agree that it would be much more convenient for them to be able to see even a limited field of view under ordinary illumination with the shell down, and it would be especially advantageous to have peripheral vision with the shell down when the arc or flame is initiated. This will minimize the risks during lifting and lowering the shell, and make the welder more aware of his surroundings. It will decrease his sense of isolation, and increase his safety. The need frequently to accommodate to different levels of illumination and the need to reorient oneself immediately before and after an arc or flame is initiated can be very bothersome. However, to provide these advantages will require a light path which is open when the flame and arc are initiated.

It is an object of this invention to provide a welder's helmet with both a conventional window fitted with welder's glass, and with auxiliary vision means which will permit the welder to look outside his helmet under all operating conditions, and which therefore is much less dark, if it is dark at all.

BRIEF DESCRIPTION OF THE INVENTION

This invention is carried out in combination with a conventional welder's helmet provided with a central window for direct viewing of the work. This window is fitted with welder's glass suitable for use in welding and cutting operations.

Auxiliary vision means according to this invention comprises at least one and preferably two wide angle negative lenses disposed laterally sidwardly of the central window. Each has a substantial field of view and a negative enlargement which has the optical effect of apparently placing a nearby object visually at least about 30 feet away, and preferably even farther.

According to yet another preferred but optional feature of the invention, the auxiliary vision means may incorporate means having a dye which prevents the transmission of most blue light and of substantially all ultraviolet light, thereby further protecting the welder, but transmitting much, if not most, of the harmless light that is useful for good vision.

The above and other features of this invention will be fully understood from the following detailed description and the accompanying drawings, in which:

BRIEF DESCRIPTION OF THE DRAWINGS

FIG. 1 is a cross-section taken at line 1—1 in FIG. 3 showing the optical system of the instant invention;

FIG. 2 is a front view of the welder's helmet shown in FIG. 1;

FIG. 3 is a side view of FIG. 2; and

FIG. 4 is an axial cross-section of one of the auxiliary optical systems taken at line 4—4 in FIG. 1.

DETAILED DESCRIPTION OF THE INVENTION

In FIGS. 1-3, there is shown a conventional welder's helmet 10 including a headband 11 with a band portion 12 to fit around the forehead and a strap 13 to fit over the top of the head. Pivots 14, 15 are provided at each side of the headpiece pivotally to mount a shell 16 to it. In accordance with conventional practice, the shell may be placed down in front of the operator's face as shown in FIG. 3 or tilted upward above his head out of the line of sight.

In accordance with conventional construction, the shell (sometimes called a hood) is opaque and is provided with a window 17 on the central axis 18 of the helmet. Such windows are customarily only large enough for the welder to view the work through it, and are occupied by a piece of welder's glass 19 such as Crook's Glass which is especially formulated to reduce the transmissivity through the window and also to absorb substantially all ultraviolet and most of the blue light from the work. The work where the welding arc or flame is to occur is shown at point 20, and is generally about 1 to 2 feet from the operator's eyes depending on the length of the operator's arms and the dimensions of the equipment that he is working with.

The shell includes side walls 21,22 which protect the welder from the glare of arcs and flames at the side. They completely interrupt his peripheral vision.

This invention provides one, but preferably two, auxiliary vision paths 25,26. Because they are identical, only path 25 will be described in detail. It is an object of these paths to permit the welder to view his surroundings, and even the work, under ordinary ambient light conditions. It is also an object of the invention for these light paths to be "open" even when the welding arc or flame is initiated.

Path 25 includes a lens system 30 which is best shown in FIG. 4. It is fitted into a cylindrical holder 31 that has an elastomeric sleeve 32 which snugly fits into a port 33 in the shell. A depth-limiting nut 34 can be provided to keep it from falling out. This nut could also be utilized as a tightening device to bear against and to enlarge the sleeve to make a tighter fit if desired. The elastomeric sleeve enables the system to be removed and replaced for repair or cleaning, and also allows for significant adjustments in direction of the central axis of the paths, merely by moving the holder in the post. He can move it around manually to adjust his field while working, so as to concentrate on different, selected regions, and FIG. 4 shows this.

Lenses of poor quality, i.e., one that produces a fuzzy image can be used to advantage because they will enlarge the welding "spot", without increasing the amount of energy that reches the eyes.

The lens system is a strongly reducing system which preferably will cause the distance of an object about 2 to 3 feet away to appear to be between about 30 and 100 feet away. The preferable apparent "distance" is about 35 feet away. Such a reducing lens system is shown in FIG. 4. A pair of back-to-back plano-concave lenses 35,35a are fitted into the holder and is nearer the work, and a plano convex lens 36 is closer to the eyes. The plano-convex lens has approximately a 45 mm focal length and a 16 mm diameter. Each plano-concave lens has a prescription of −2.2 diopters, having a 21 mm diameter and a 9 mm radius on the concave side. The planar faces of lenses 35a and 36 are spaced approximately 3 cm apart. This system will cause a marked reduction not only in the size of the object being viewed, to which reduction the welder can quickly become accustomed, but also reduces the intensity of the arc or flame even when viewed through this lens to a size and quantum which can be tolerated by the welder.

In addition, it is advantageous but optional to provide a filter plate and spatter shield 37 in or ahead of the lens system. These features may be combined into the single plate and may conveniently be a plastic plate dyed with a dye having the property of absorbing the ultraviolet wavelengths and most of the blue light. Dyes for this purpose are conventionally incorporated into welding curtains and such dyes and such materials are fully shown in Miller and Stephens U.S. Pat. No. 4,330,177, issued May 18, 1982, assigned to the same assignee as the instant invention. This patent is incorporated herein by reference for its disclosure of suitable dyes (generally orange colored) for this purpose.

Speaking generally, a yellow dye with a cut-on at about 450 nm, or an orange eye with a cut-on at about 500 nm will be preferred. Ultraviolet absorbers, which are conventional might also be added if the dye does not sufficiently absorb in the ultraviolet range. By "cut-on" is meant that wavelengths shorter than the cut-on value are mainly absorbed, and there is substantial transmission of visible wavelengths above the cut-off value. Generally, at least 99% absorption of ultraviolet is to be preferred.

The auxiliary vision paths have respective central axes 40, 41 which look away from the central axis. Each of them has a field of view shown by boundary lines 42, 43 and 44,45. Lines 43 and 44 represent the inward excursion of the fields of view, and it will be noted that they preferably pass behind the work. Then when the welder looks directly at the work, light from the work will not directly enter the auxiliary system. The field of view is preferably quite wide, exceeding 90° if possible, in order that the peripheral view as defined by lines 42 and 45 exceeds 180°. Then the welder has an adequate peripheral field of vision to protect himself and to react to his surroundings. Of course he can turn his head to look in any direction through the systems. The systems are located within the ready view of the welder's eyes because he cannot turn his head relative to them. The plate can be partially be masked if one wishes to reduce the field.

By providing a suitably large reduction in image with a suitable use of reduction lenses, the welder can utilize the auxiliary vision paths even without concern for reduction of transmissivity. The quantum and brightness of the welding spot will be suitably reduced. An apparent "distance" of 30 feet or more appears to reduce the brightness and energy quantum of the arc or flame to the eye that it can be looked at even without the dye. It is even more favorable with the dye, and with a large apparent distance. However, utilizing the dyed filter plate provides an extra margin of safety by filtering out all of the UV radiation and most of the more dangerous blue wavelengths of visible light. If only splatter protection is desired, the plate need not include a dye. At transparent poly carbonate plate is to be preferred.

This invention thereby provides a welding helmet in which the welder can at all times see his surroundings whether or not the arc or flame is initiated, and look through the auxiliary system safely to work on his set up even without raising his helmet. He will at all times be protected from other nearby arcs and flames. The plate can be dyed, and effectively resists burning by spatter.

The term "reducing" implies also an expanded field of vision.

This invention is not to be limited by the embodiments shown in the drawings and described in the description which are given by way of example and not of limitation, but only in accordance with the scope of the appended claims.

We claim:

1. In a welding helmet comprising a shell mountable to a welder's head, said helmet having an opaque wall extending in front of and to the sides of the welder's face to shield him from a welding arc or flame in front of him, and from arcs or flames to the side of him, said shell having a window occupied by a welder's glass to enable the welder to look forwardly along a forward axis at work in front of him while an arc or flame is burning, the improvement comprising:

to the side of said window and passing through said wall, a reducing auxiliary vision system through said helmet having the optical property of reducing an object which is located about 30 inches from the hood to an apparent distance significantly greater than the distance to said object, said auxiliary system having an optical axis directed at an angle to said forward axis, whereby to provide visibility under normal illumination of regions substantially to the side of said forward axis.

2. A welding helmet according to claim 1 in which said apparent distance is at least 30 feet.

3. A welding helmet according to claim 1 in which said auxiliary vision system has a viewing angle of at least about 90°.

4. A welding helmet according to claim 1 in which said viewing angle does not include the work when the work is about 30 inches from the window and directly in front of the helmet.

5. A welding helmet according to claim 1 in which a filter is placed in said vision system having the property of filtering out substantially all ultraviolet, and most blue light.

6. A welding helmet according to claim 1 in which each vision system includes, exposed to the object, a transparent plate to receive and resist spatter.

7. A welding helmet according to claim 6 in which said plate is made of polycarbonate material.

8. A welding helmet according to claim 1 in which each said vision system is fitted in a respective port through said wall, in which it is adjustably movable.

9. A welding helmet according to claim 1 in which said vision systems include at least one lens of relatively poor surface quality so as to fuzz the image.

10. A welding helmet according to claim 5 in which said filter is colored orange.

11. A welding helmet according to claim 1 in which there is a pair of said auxiliary vision systems, one on each side of said window.

12. A welding helmet according to claim 11 in which each said vision system has a viewing angle of at least about 90°.

13. A welding helmet according to claim 11 in which the fields of said viewing angle do not include the work when the work is about 30 inches from the window.

14. A welding helmet according to claim 1 in which a mask is provided to cover at least a portion of the entry aperture to each said vision system.

15. A welding helmet according to claim 11 in which a filter is placed in said vision system having the property of filtering our substantially all ultraviolet, and most blue light.

16. A welding helmet according to claim 15 in which said filter is colored orange by a dye which cuts on at approximately 500 nm.

17. A welding helmet according to claim 15 in which said filter is colored yellow by a dye which cuts on at approximately 450 nm.

* * * * *